(12) United States Patent
Steinlauf (10) Patent No.: US 11,911,081 B2
(45) Date of Patent: Feb. 27, 2024

(54) CALCANEAL CROSS MEDULLARY PLATE (71) Applicant: Extremity Medical, LLC, Parsippany, NJ (US)

(72) Inventor: Steven D. Steinlauf, Weston, FL (US)

(73) Assignee: EXTREMITY MEDICAL LLC, Parsippany, NJ (US)

( * ) Notice: Subject to any disclaimer, the term of this patent is extended or adjusted under 35 U.S.C. 154(b) by 115 days.

(21) Appl. No.: 17/346,257

(22) Filed: Jun. 13, 2021

(65) Prior Publication Data

US 2021/0298802 A1    Sep. 30, 2021

Related U.S. Application Data

(63) Continuation of application No. 15/920,419, filed on Mar. 13, 2018, now Pat. No. 11,033,303.

(60) Provisional application No. 62/470,472, filed on Mar. 13, 2017.

(51) Int. Cl.
*A61B 17/72* (2006.01)
*A61B 17/80* (2006.01)

(52) U.S. Cl.
CPC ...... *A61B 17/7233* (2013.01); *A61B 17/8061* (2013.01); *A61B 17/7291* (2013.01)

(58) Field of Classification Search
CPC ...... A61B 17/7059; A61B 17/72–7291; A61B 17/80–8095
See application file for complete search history.

(56) References Cited

U.S. PATENT DOCUMENTS

| | | | |
|---|---|---|---|
| 6,139,550 A * | 10/2000 | Michelson | A61B 17/80 606/295 |
| 7,780,710 B2 * | 8/2010 | Orbay | A61B 17/8061 606/310 |
| 8,182,485 B1 | 5/2012 | Gonzalez-Hernandez | |
| 8,361,075 B2 | 1/2013 | Gonzalez-Hernandez | |
| 8,574,234 B2 | 11/2013 | Gonzalez-Hernandez | |
| 8,574,270 B2 | 11/2013 | Hess et al. | |
| 8,974,504 B2 | 3/2015 | Hess et al. | |
| 9,005,255 B2 | 4/2015 | Lewis et al. | |
| 9,017,329 B2 | 4/2015 | Tyber et al. | |
| 9,044,282 B2 | 6/2015 | Tyber et al. | |
| 9,066,768 B2 * | 6/2015 | Weiner | A61B 17/8033 |
| 11,033,303 B2 * | 6/2021 | Steinlauf | A61B 17/7233 |
| 2005/0165395 A1 * | 7/2005 | Orbay | A61B 17/8061 606/60 |
| 2006/0142763 A1 | 6/2006 | Munro et al. | |
| 2007/0225714 A1 * | 9/2007 | Gradl | A61B 17/746 606/326 |
| 2008/0300637 A1 * | 12/2008 | Austin | A61B 17/8605 606/290 |

(Continued)

*Primary Examiner* — Eduardo C Robert
*Assistant Examiner* — Steven J Cotroneo
(74) *Attorney, Agent, or Firm* — Kelley Drye & Warren LLP (57) ABSTRACT

Apparatus and method for securely fixating an anterior portion of a calcaneus to a reduced posterior facet portion of the calcaneus, using a plate that may allow for stable fixation between the anterior calcaneus, the reconstructed posterior facet, and the posterior tuberosity, and a barrel that may be rotated into the best position to allow posterior screws to enter the best quality bone in the posterior tuberosity. The appropriate height may be set by rotating a push screw, thereby engaging the barrel, and pushing the posterior tuberosity distally.

16 Claims, 13 Drawing Sheets

(56) References Cited

U.S. PATENT DOCUMENTS

| | | | |
|---|---|---|---|
| 2011/0060373 A1* | 3/2011 | Russell | A61B 17/8875 606/86 R |
| 2011/0137313 A1* | 6/2011 | Jensen | A61B 17/72 606/64 |
| 2012/0010719 A1* | 1/2012 | Reiley | A61F 2/4606 623/21.18 |
| 2012/0083848 A1 | 4/2012 | Gonzalez-Hernandez | |
| 2012/0226322 A1 | 9/2012 | Gonzalez-Hernandez | |
| 2013/0116734 A1 | 5/2013 | Gonzalez-Hernandez | |
| 2016/0256204 A1* | 9/2016 | Patel | A61B 17/8061 |
| 2017/0020569 A1* | 1/2017 | Grant | A61B 17/8057 |

* cited by examiner

CALCANEAL CROSS MEDULLARY PLATE

CROSS REFERENCE TO RELATED APPLICATION

This application is a continuation of U.S. patent application Ser. No. 15/920,419, filed on Mar. 13, 2018, which claims the benefit of U.S. Provisional Patent Application No. 62/470,472, filed Mar. 13, 2017. The entire contents of these applications are incorporated herein by reference.

FIELD OF THE INVENTION

This invention relates to the field of implant devices for bone fixation.

BACKGROUND OF THE INVENTION

The calcaneus is the most frequently fractured tarsal bone. In the majority of cases, the calcaneus breaks into three main fragments, namely the anterior, posterior facet, and posterior tuberosity. The posterior facet is the main joint surface and is often broken into two or more pieces. To successfully repair a calcaneus that is fractured, the posterior facet joint surface typically should be accurately reduced and securely fixated. The posterior facet is then typically securely fixated to the anterior portion and the posterior tuberosity, restoring the normal alignment of the body of the calcaneus. The majority of calcaneus fractures are fixed with a plate placed on the lateral aspect of the calcaneus or the medial aspect of the calcaneus, and screws are usually placed through the plate to fixate the plate to the calcaneus. Independent lag screws are often used to bring the joint surfaces together. Some newer concepts involve an intramedullary nail placed along the longitudinal or long axis of the calcaneus with interlocking screws placed through the nail with the use of Jiggs. Finally, independent lag screws can be used, and external fixation can be used. However, a need exists for a plate coupled with an intramedullary device.

Some of the main complications of open treatment and internal fixation of calcaneus fractures are poor wound healing and infection. Secondary complications include stiffness due to extensive scarring after internal fixation requiring extensive elevation of soft tissue envelopes. Although some of the existing devices assert that a patient can bear weight early after internal fixation, there is no good data to support immediate weight bearing with any of the current devices.

In particular, placing a plate over either the lateral aspect or medial aspect of the calcaneus typically requires significant surgical approaches and elevation of soft tissues, even with a smaller sinus tarsi approach. This extensive elevation of soft tissue off the calcaneal bone may lead to disruption of the blood supply to the bone and may compromise the viability of the soft tissues. Such results then lead to the higher risk of scarring, poor wound healing, and infections.

One solution would be to place everything intramedullary (i.e., in the middle of the calcaneus). However, such solution does not typically allow for adequate reduction and stabilization of the posterior facet, which is the articular surface of the subtalar joint. If the joint surface is not accurately and securely fixated, the risk of developing post traumatic arthritis is greatly increased. Therefore, the concept of using an intramedullary device should be coupled with an open approach to accurately reduce the joint fracture and then to fixate the joint with independent screws. However, the intramedullary device and the independent lag screws may not be coupled together. This allows for accurate reduction of the joint and the body of the calcaneus, but does not provide for adequate axial stability to permit early weight bearing.

The current intramedullary products on the market do not allow for accurate joint fixation. The current screw and plate products on the market usually lead to excessive soft tissue injury and higher wound healing and infection risks. Thus, there is a need for a device that will provide for less invasive accurate fixation and for adequate stability.

SUMMARY OF THE INVENTION

The present invention is directed to a combination of a limited plating technique through a small incision with intramedullary screw fixation engaging a barrel.

It is an object of the present invention to reduce elevation of soft tissue, leading to less devitalization, less scarring, improved range of motion, enhanced function, and a lower infection rate compared to traditional extensile lateral plating.

It is a further object of the present invention to allow for accurate, stable joint restoration which may lead to a lower risk of post traumatic arthritis.

Numerous variations may be practiced in the preferred embodiment.

BRIEF DESCRIPTION OF THE DRAWINGS

A further understanding of the invention can be obtained by reference to embodiments set forth in the illustrations of the accompanying drawings. Although the illustrated embodiments are merely exemplary of systems, methods, and apparatuses for carrying out the invention, both the organization and method of operation of the invention, in general, together with further objectives and advantages thereof, may be more easily understood by reference to the drawings and the following description. Like reference numbers generally refer to like features (e.g., functionally similar and/or structurally similar elements).

The drawings are not necessarily depicted to scale; in some instances, various aspects of the subject matter disclosed herein may be shown exaggerated or enlarged in the drawings to facilitate an understanding of different features. Also, the drawings are not intended to limit the scope of this invention, which is set forth with particularity in the claims as appended hereto or as subsequently amended, but merely to clarify and exemplify the invention.

DETAILED DESCRIPTION OF THE INVENTION

The invention may be understood more readily by reference to the following detailed descriptions of embodiments of the invention. However, techniques, systems, and operating structures in accordance with the invention may be embodied in a wide variety of forms and modes, some of which may be quite different from those in the disclosed embodiments. Also, the features and elements disclosed herein may be combined to form various combinations without exclusivity, unless expressly stated otherwise. Consequently, the specific structural and functional details disclosed herein are merely representative. Yet, in that regard, they are deemed to afford the best embodiment for purposes of disclosure and to provide a basis for the claims herein, which define the scope of the invention. It must be noted that, as used in the specification and the appended claims, the singular forms "a", "an", and "the" include plural referents unless the context clearly indicates otherwise.

The invention is described herein with reference to repair of a fractured calcaneus. The plate portion of the present device may securely fixate the anterior portion of the calcaneus (1) to the reduced posterior facet/joint portion of the calcaneus and then may integrate with the intramedullary portion of the device to provide enhanced stability between all three major portions of the calcaneus.

The device may be installed by using an open approach through the sinus tarsi, allowing direct vision of the joint surface, so that the posterior facet can be accurately reduced and stabilized with independent lag screws. A plate (4) may allow for stable fixation between the anterior calcaneus (1), the reconstructed posterior facet (19), and the posterior tuberosity (3) without (or with minimal) stripping away of the blood supply to the posterior calcaneus. One of the benefits of having the screws coming from the posterior tuberosity (3) and locking into the barrel (9) of the plate (4) is that the patient will have excellent early stability and can bear weight early. In various embodiments, the screws fixating the posterior tuberosity to the intramedullary barrel may make it possible to eliminate (or reduce the use of) the posterior plate portion of all existing plating products, preserving the posterior lateral soft tissues. This would lead to a lower infection risk and improved healing.

Figures 1, 1A, 1B:
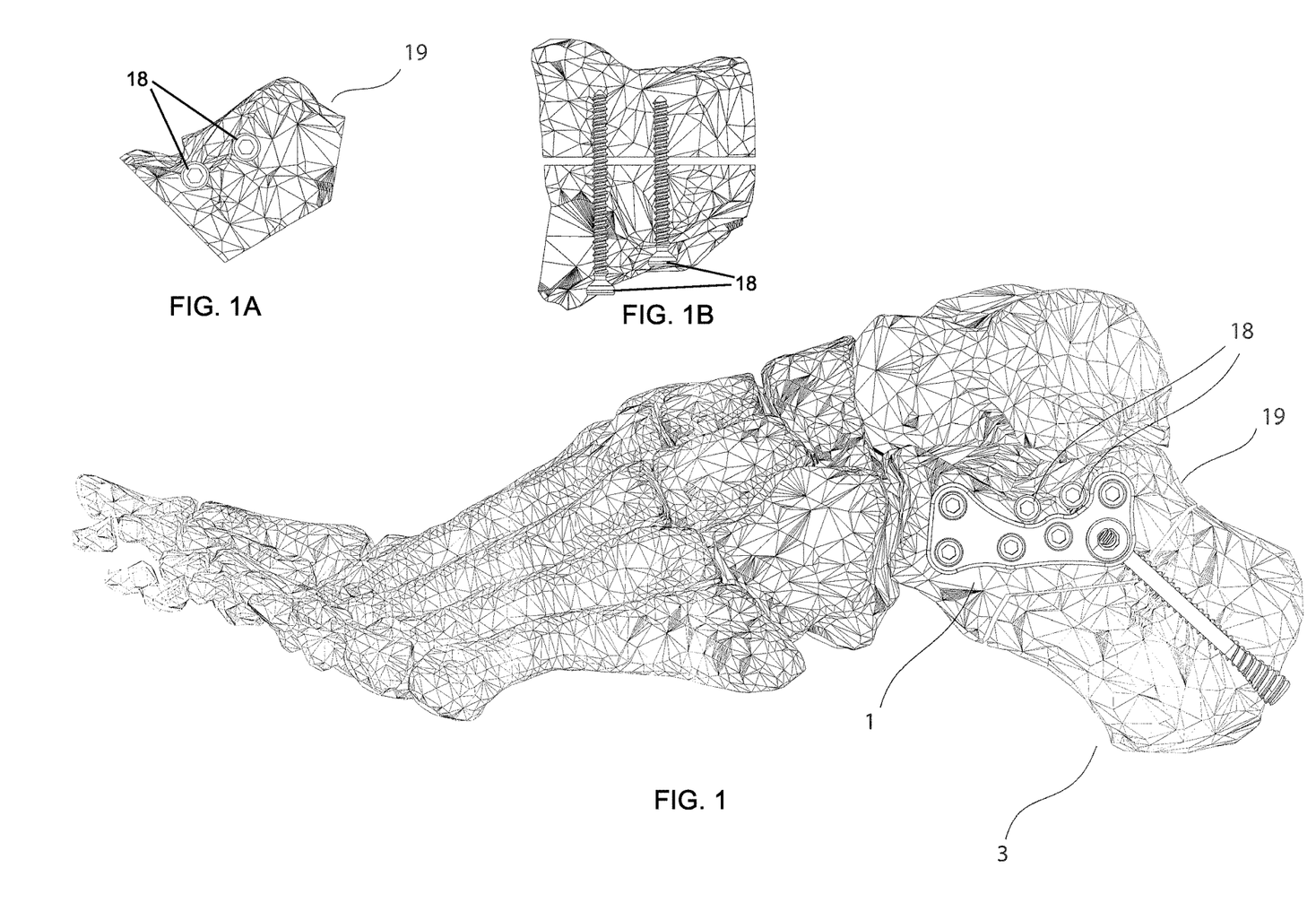
FIG. 1 depicts a plate fixating 3 major portions of calcaneus.
FIG. 1A depicts a posterior facet fracture from the side with independent lag screws.
FIG. 1B depicts a posterior facet fracture from above with independent lag screws.
Figure 2:
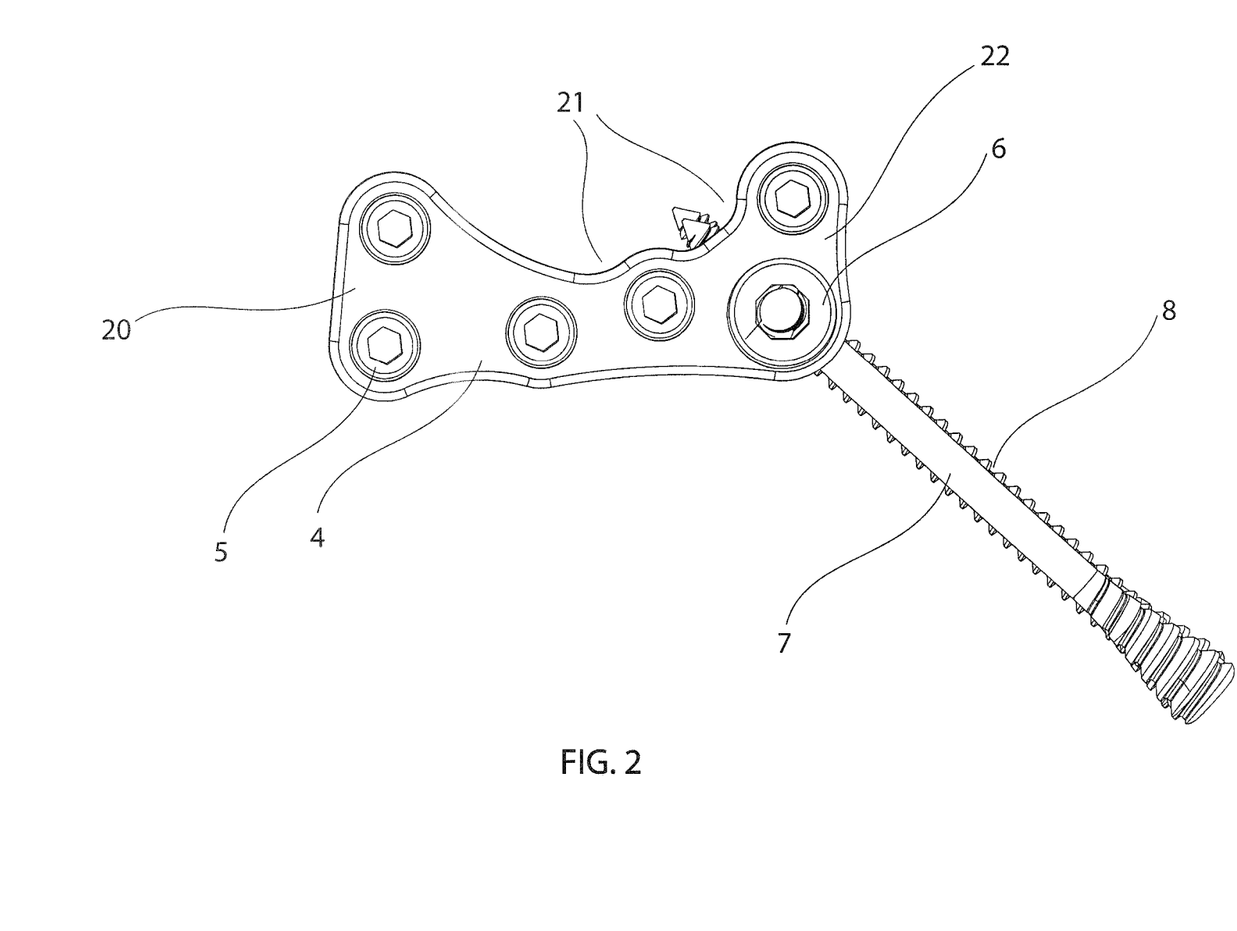
FIG. 2 depicts a front view of a calcaneal plate with cross medullary fixation system.

In various embodiments, and during surgery, the surgeon may place a medial temporary external fixator to bring the calcaneus out to an appropriate height. This may make reduction of the posterior facet easier. The surgeon may utilize a sinus tarsi approach from the tip of the fibula to the anterior process of the calcaneus. The surgeon may elevate the peroneal tendons off of the anterior calcaneus and the region below the posterior facet. As shown in FIG. 1, this is where the plate may be placed. Prior to placing the plate, the posterior facet may be reduced and stabilized with either small independent wires or screws (18). As shown in FIG. 2, plate (4) may extend from an anterior end (20) to a posterior end (22) and may have one or more scalloped cutouts to facilitate implantation of screws (18).

A template may then be placed along the lateral wall after dis-impacting the fracture of the lateral wall. Once the appropriate plate size is determined, the definitive plate (4) may be placed. As shown in FIG. 1, the plate may securely fixate the anterior calcaneus (1) to the reconstructed posterior facet (19).

The surgeon may drill a hole through the calcaneus for barrel (9), and then barrel (9) may be placed. A stepped portion (12) at the top of barrel (9) may mate with a recess within aperture (36) through which barrel (9) is placed. A flange (11) on the side of plate (4) facing the bone may be used to axially support barrel (9). Flange (11) may partially or entirely encircle aperture (36).

Figure 3:
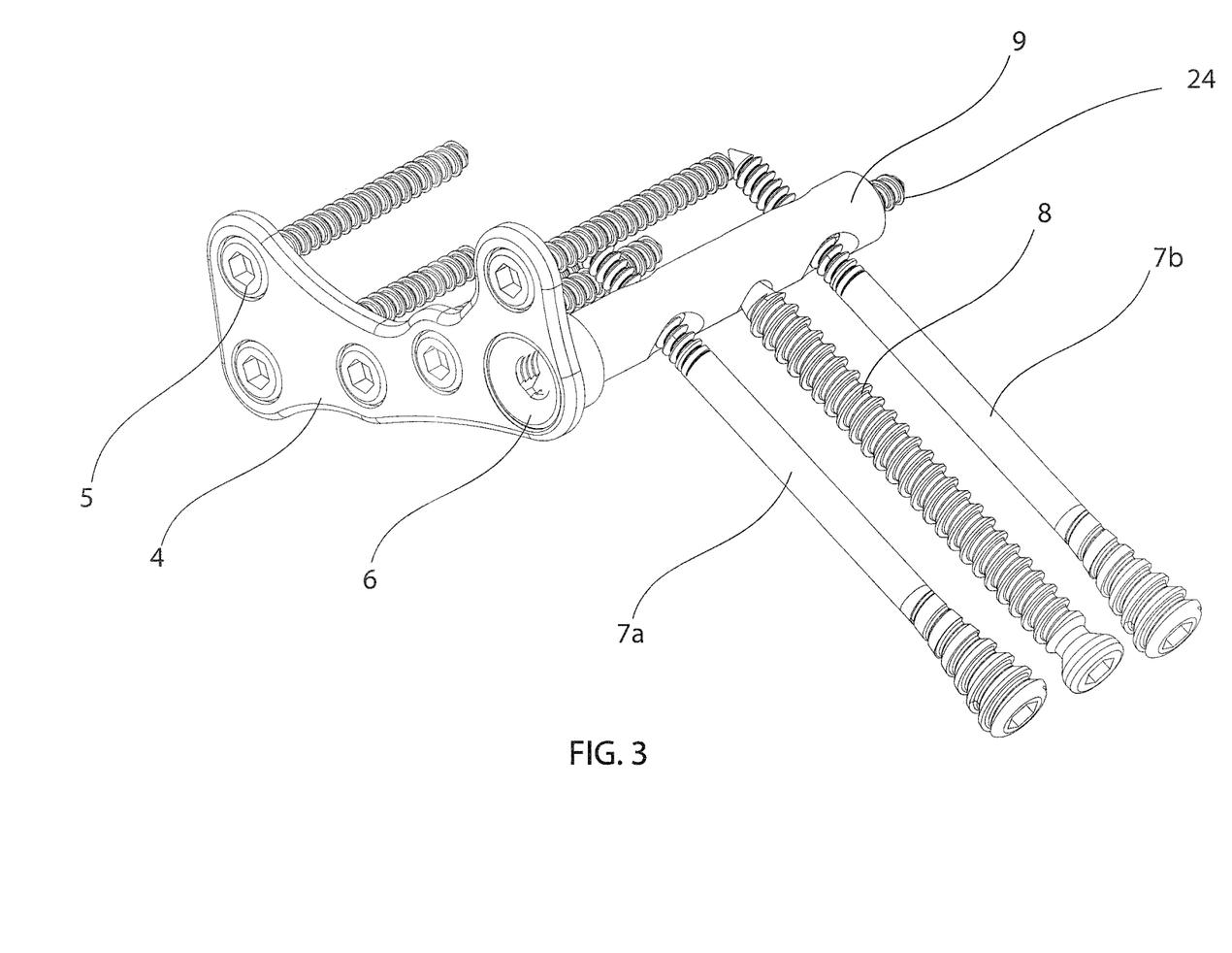
FIG. 3 depicts an isometric view of a calcaneal plate with cross medullary fixation system.
Figure 4:
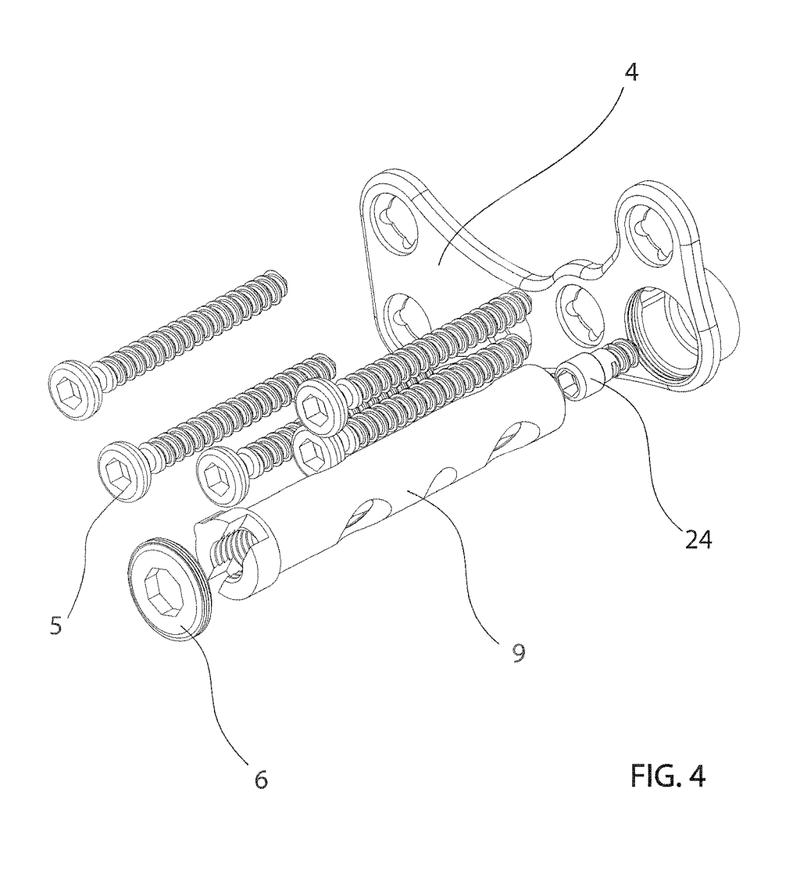
FIG. 4 depicts an exploded view of a calcaneal plate with cross medullary fixation system.
Figure 10:
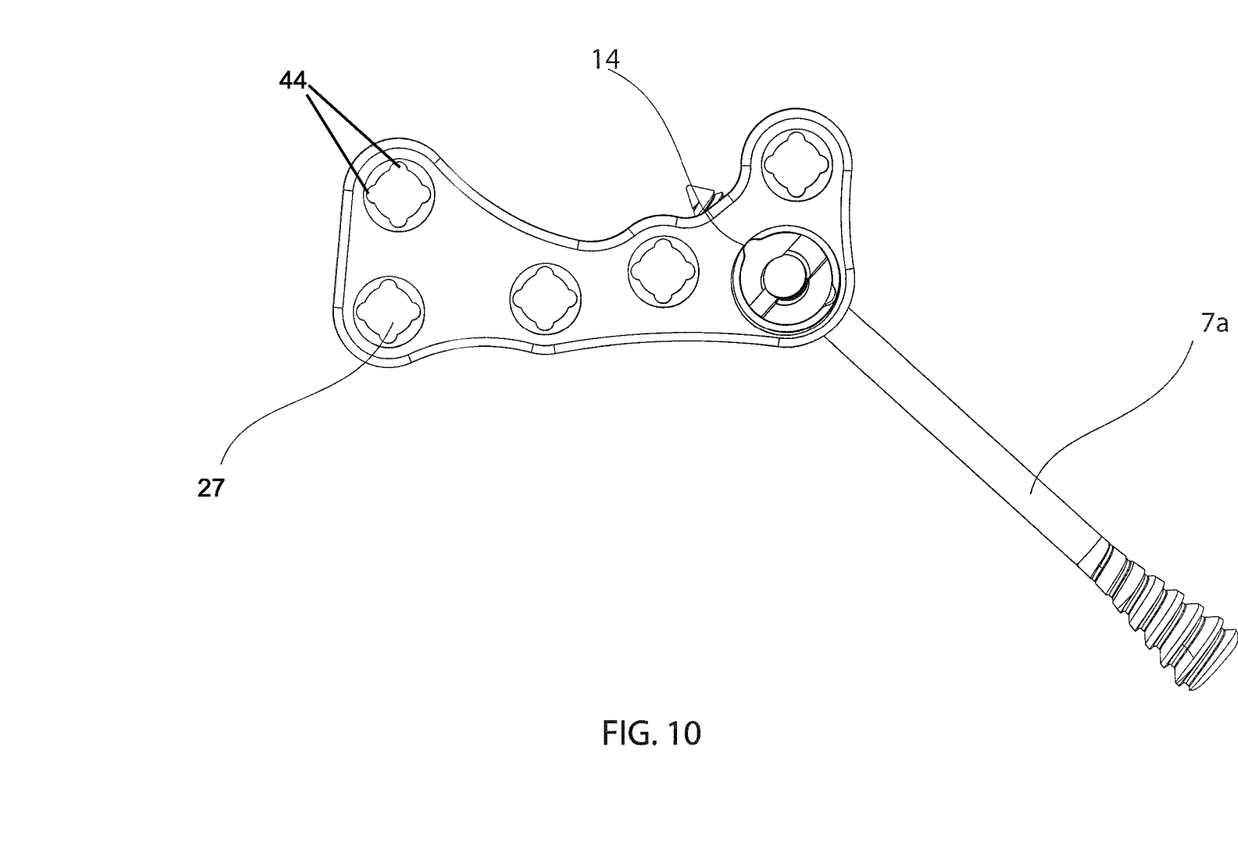
FIG. 10 depicts a plate with barrel and posterior tuberosity screw at first position.
Figure 11:
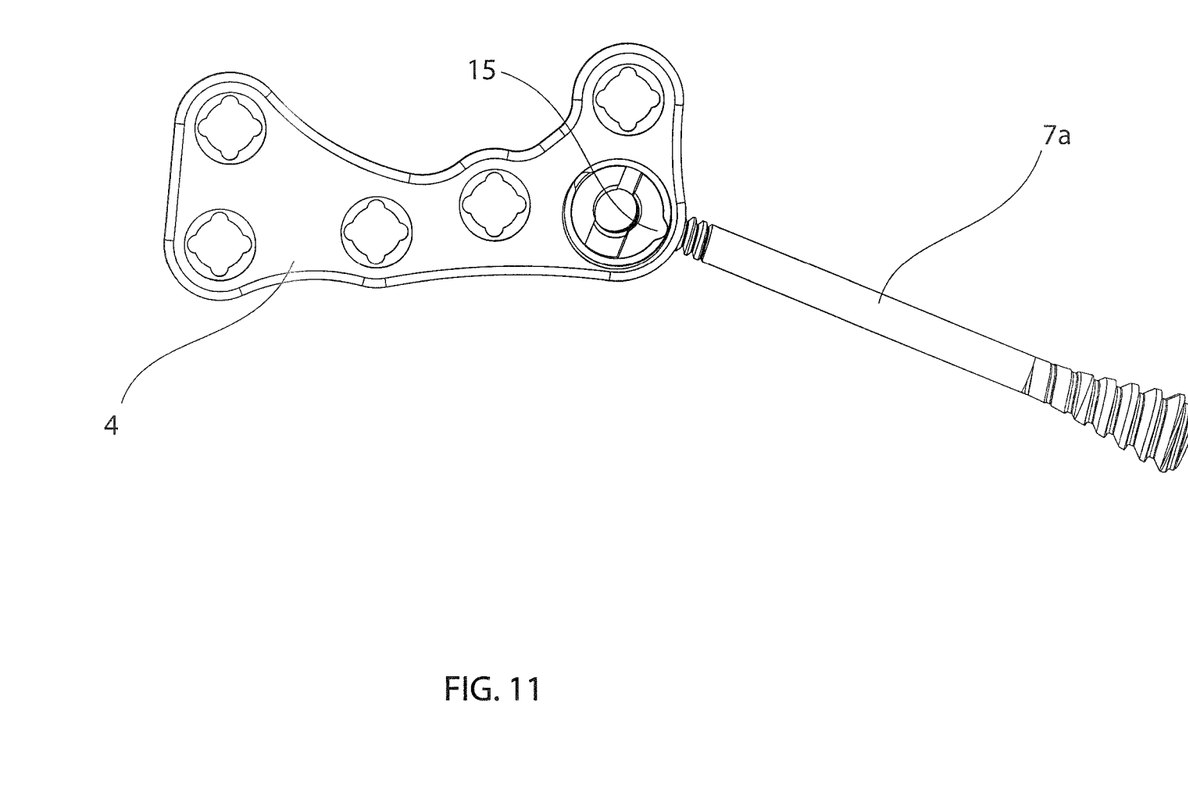
FIG. 11 depicts a plate with barrel and posterior tuberosity screw at alternate position.

Barrel (9) may be rotated into the best position to allow posterior screws to enter the best quality bone in the posterior tuberosity. FIGS. 10 and 11 show posterior screw (7a) positioned at different angles with respect to plate (4). Referring to FIGS. 8-11, barrel (9) may then be locked into position with the plate by mating one or more locking tabs (13) with indentations (14 and/or 15) in aperture (36). As seen in FIGS. 2-4, a barrel locking cap (6) may be inserted into aperture (36) on top of stepped portion (12) of barrel (9). Locking cap (6) may installed in a number of ways, including, by press fitting locking cap (6) into aperture (36), or by engaging threads on the outer circumference of locking cap (6) with threads on the interior surface of aperture (36).

Figure 12:
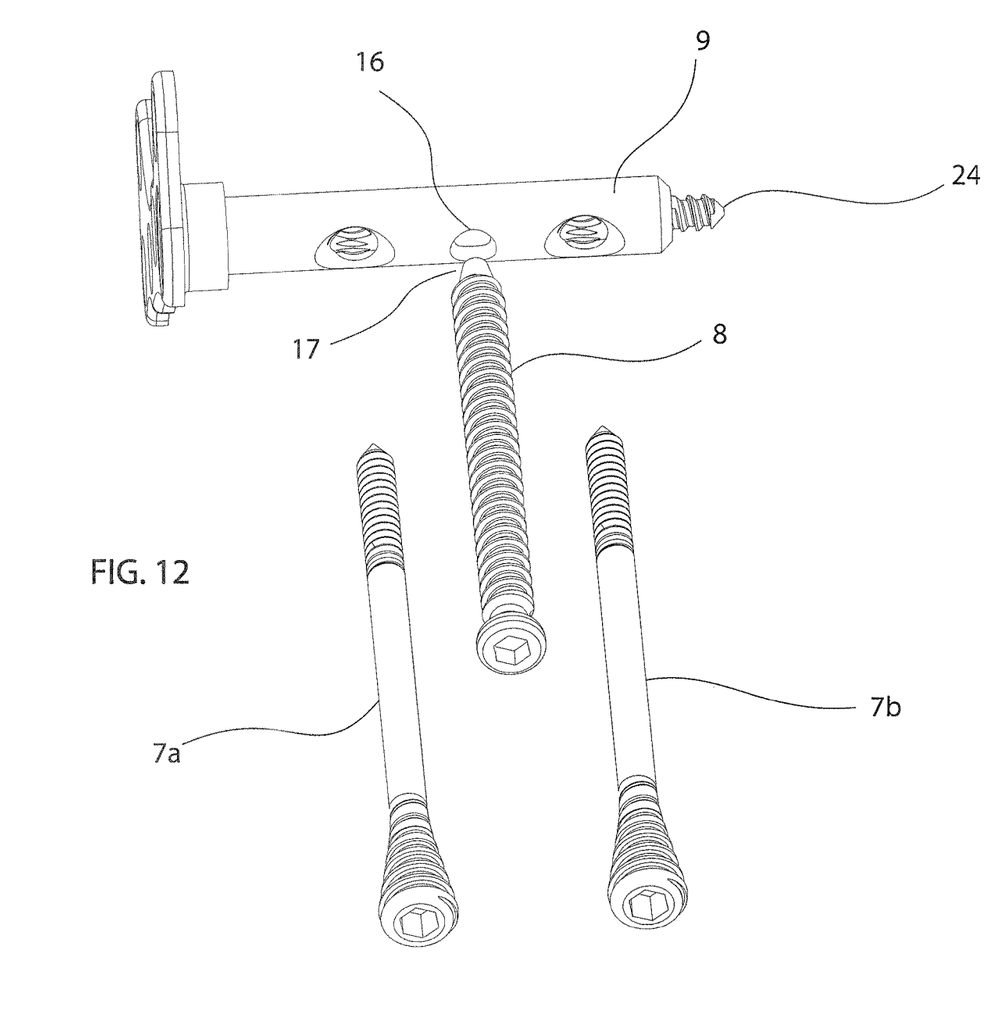
FIG. 12 depicts a calcaneal plate and barrel after initial implantation prior to fracture site repositioning.

Referring to FIG. 4, barrel (9) may be secured to the medial wall of the calcaneus with screw (24), placed through the central portion of barrel (9). Screw (24) may lock into the tip of barrel (9) as shown in FIG. 12. This may enhance the axial stability of the final construct.

A jig may be connected to the plate and reduction of the posterior tuberosity may be performed. From a unique standpoint of making the surgery easier and more reproducible, the surgeon may utilize the jig to place a half pin into the posterior tuberosity to correct the varus/valgus alignment. Once this is corrected, the pin may be locked to the jig, as long as the height is correct.

Figure 13:
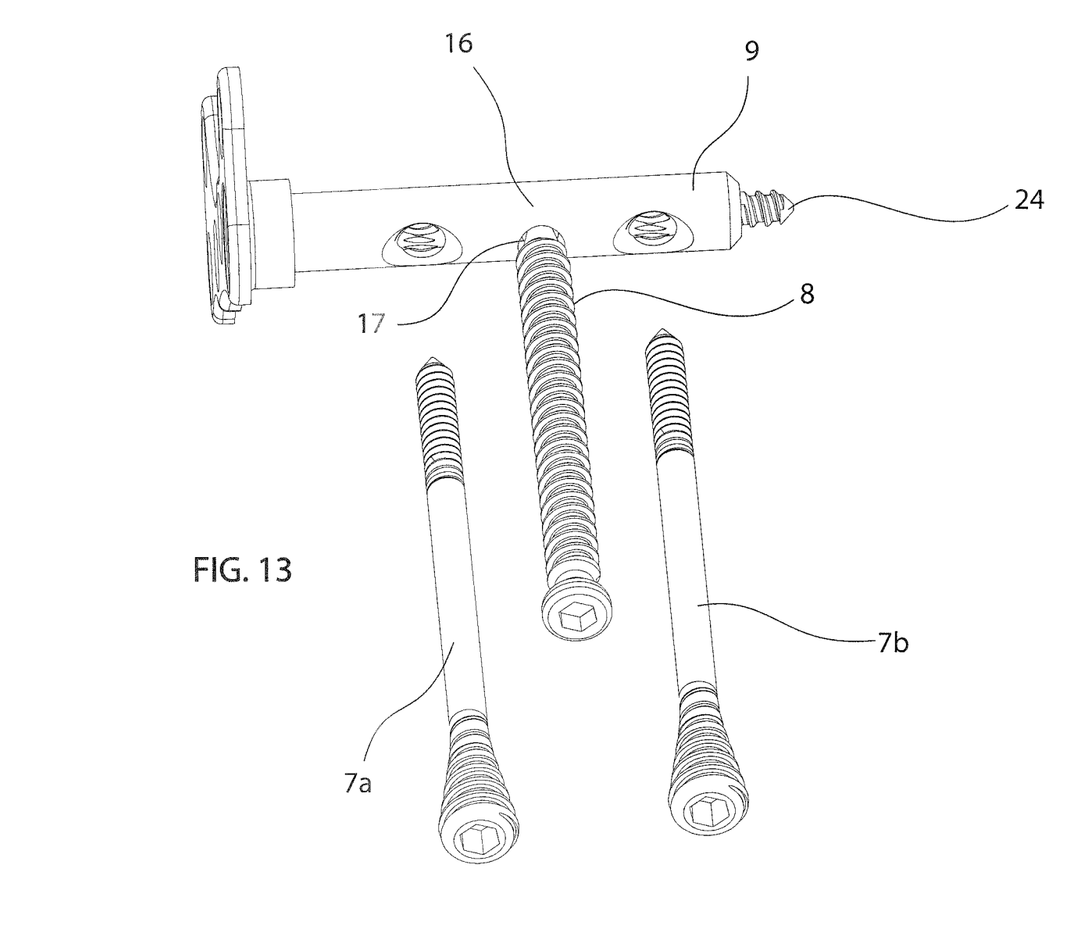
FIG. 13 depicts a calcaneal plate and barrel with push screw interfaced with barrel.
Figure 14:
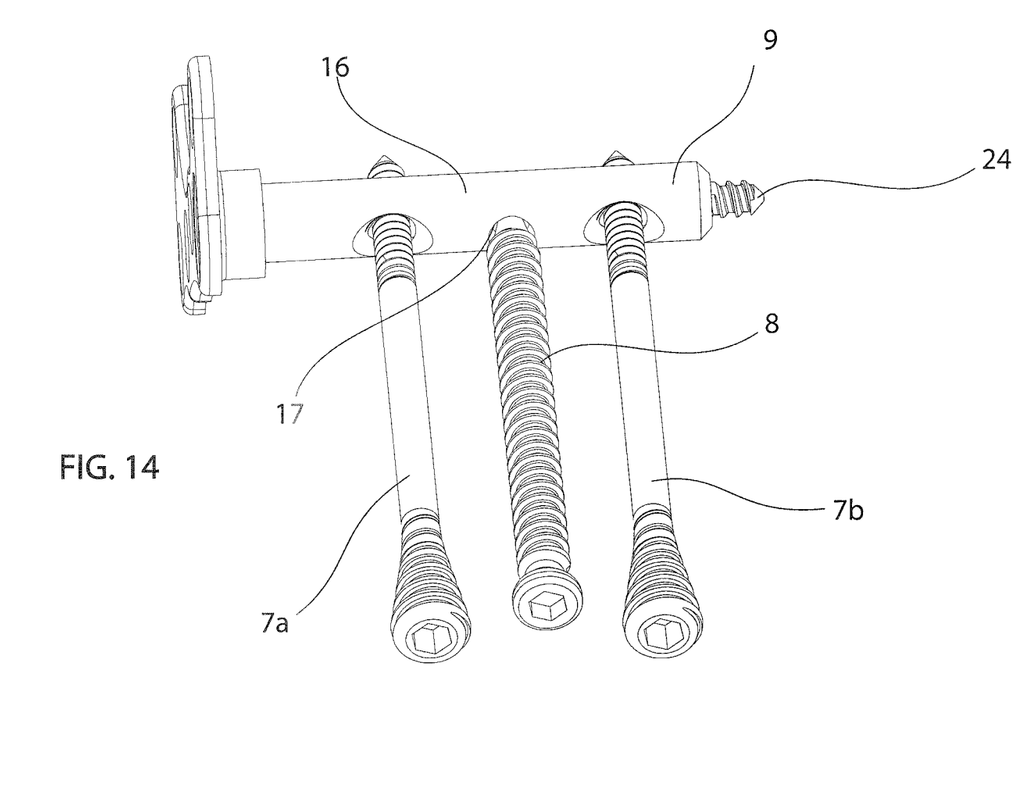
FIG. 14 depicts a calcaneal plate and barrel with push screw and posterior tuberosity screws.

As shown in FIGS. 12 and 13, if the height of the posterior tuberosity is not correct, push screw (8) may be employed. Push screw (8) may be a fully threaded screw. In the alternative, the leading end (17) of push screw (8) may be bare of threads as shown in FIG. 12. Push screw (8) may be inserted so as to make contact with barrel (9). The point of contact may be an aperture or shallow indentation (16). If two lags screws (7a, 7b) are to be inserted, for example, the shallow indentation (16) or other point of impact may be located between the apertures that receive lag screws (7a, 7b). For example, aperture (16) may be located half-way between the two lag screws (7a, 7b).

Figure 5:
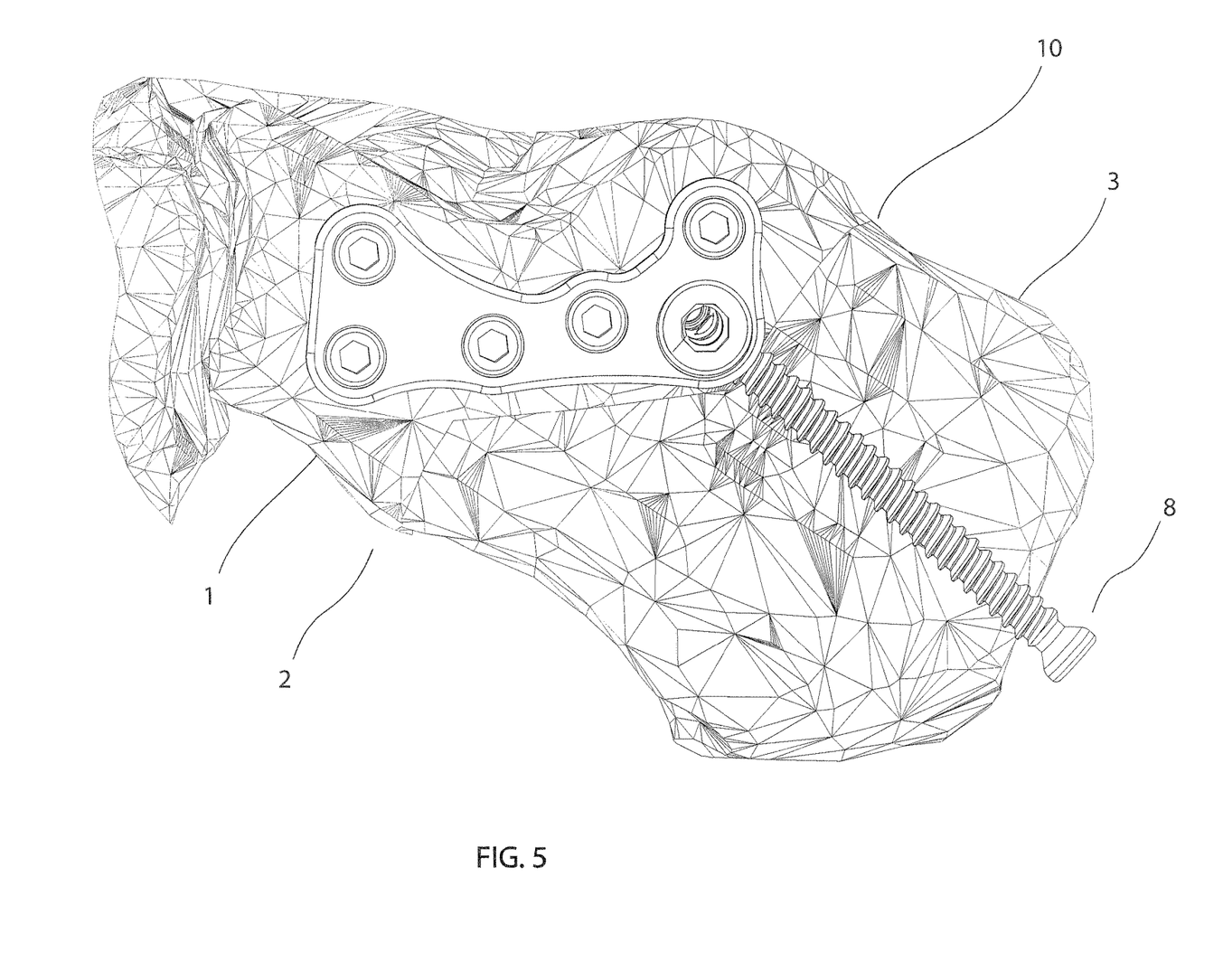
FIG. 5 depicts a fracture site in an initial position.
Figure 6:
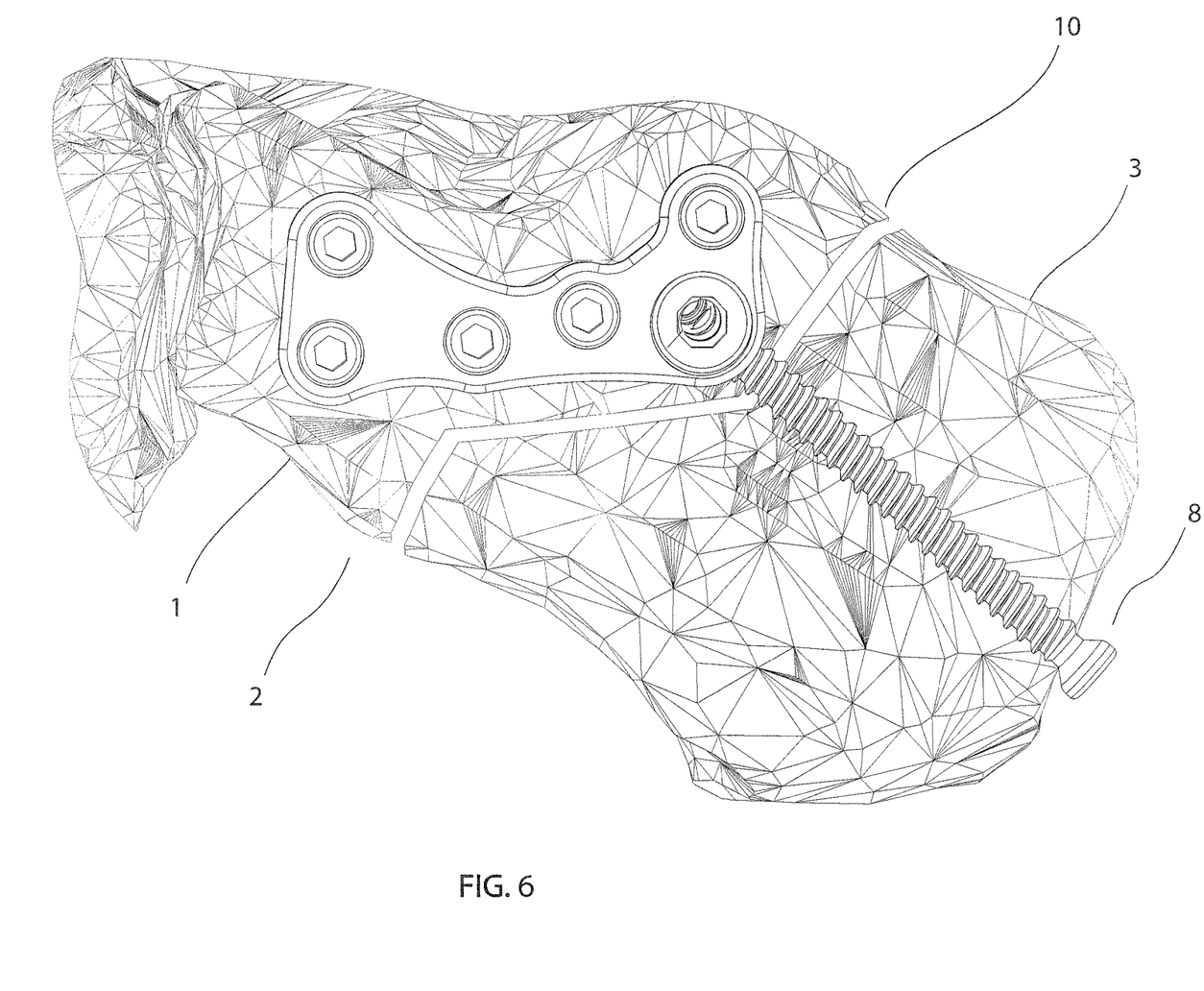
FIG. 6 depicts a fracture site brought out to appropriate height.
Figure 7:
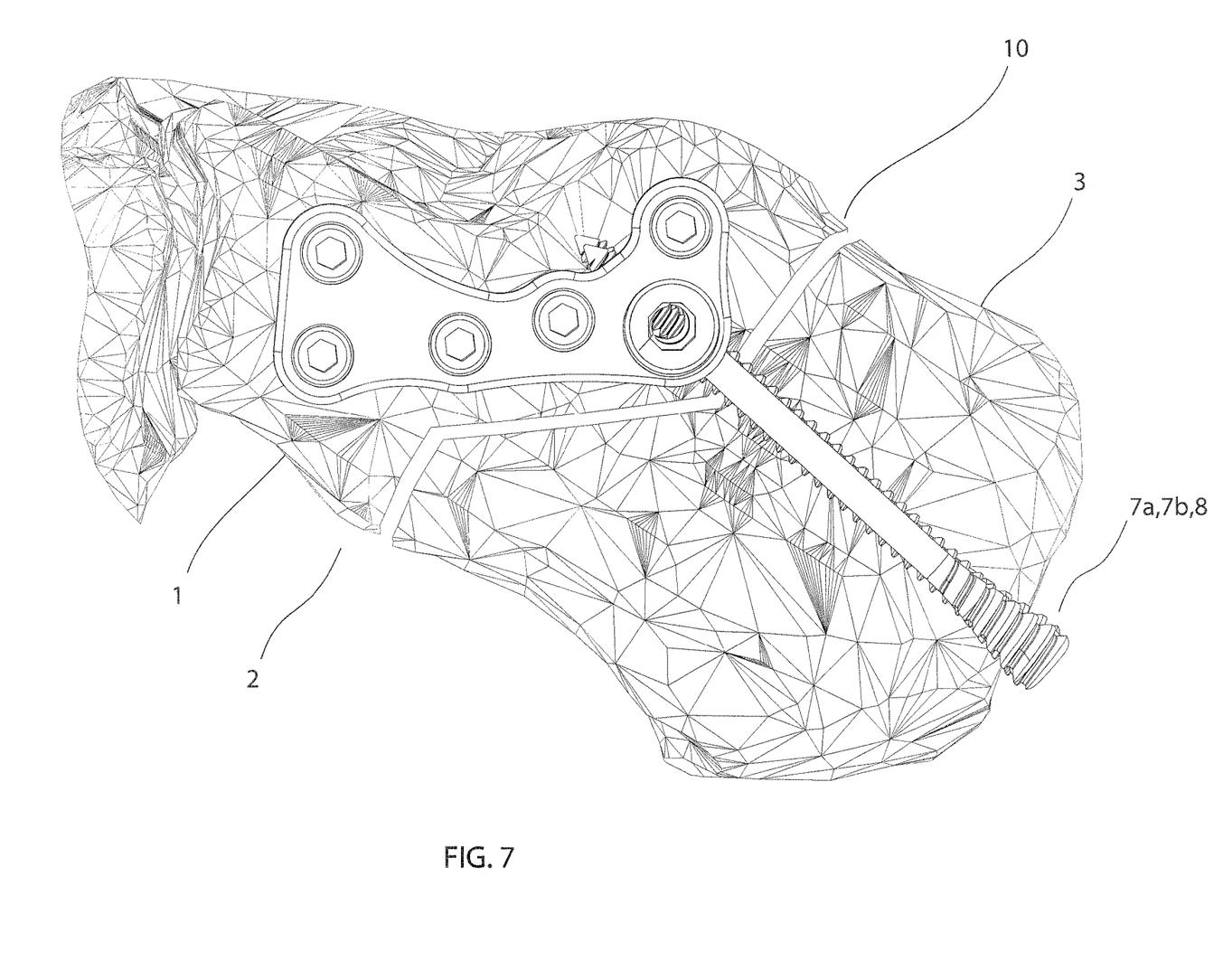
FIG. 7 depicts a fracture position fixated by posterior tuberosity screws.
Figures 8, 9:
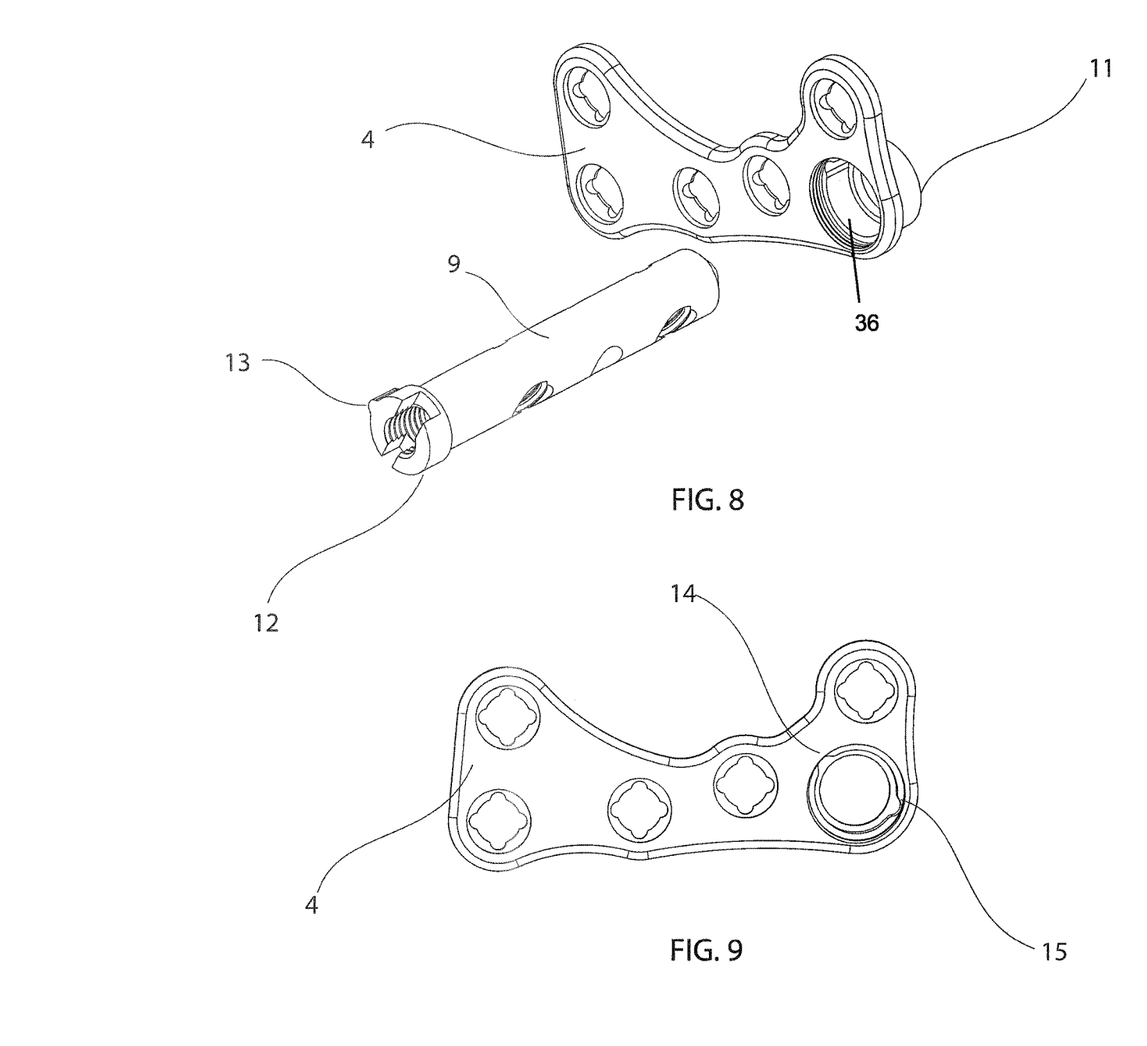
FIG. 8 depicts a plate and cross medullary barrel in axial alignment.
FIG. 9 depicts a front view of a calcaneal plate.

As seen in FIGS. 5 and 6, a surgeon may "dial" the appropriate height into the posterior tuberosity by rotating push screw (8), thereby engaging barrel (9), and pushing the posterior tuberosity distally. Once the height and alignment of the posterior tuberosity are appropriate, two screws (7a, 7b) may be placed from the posterior tuberosity into barrel (9) engaging the barrel.

As shown in FIG. 12, each of the screw (7a, 7b) may have an elongated body extending along a longitudinal axis, with a threaded portion at a first end for advancing the screw into a bone or fragment. At the other end, each screw may have a tapered head. The tapered head may also be threaded. Between the first end and the head, each screw may have an unthreaded shaft as shown in FIG. 12. In the alternative, each screw may have a threaded shaft.

On or more screws (5) may be inserted through holes (27) in plate (4). And into bone. Screws (5) may be locking or non-locking screws. As shown in FIG. 10, each hole (27) may have one or more indentations. Each heads of screws (5) may include a locking tab that allows the screw head to be locked in hole (27). Holes (27) may be arranged so that the center-lines of holes (27) do not intersect the implantation path of screws (7a, 7b), so that when screws (5) are implanted following implantation of screws (7a, 7b), screws (5) do not make contact with screws (7a, 7b).

While the invention has been described in detail with reference to embodiments for the purposes of making a complete disclosure of the invention, such embodiments are merely exemplary and are not intended to be limiting or represent an exhaustive enumeration of all aspects of the invention. It will be apparent to those of ordinary skill in the art that numerous changes may be made in such details, and the invention is capable of being embodied in other forms, without departing from the spirit, essential characteristics, and principles of the invention. Also, the benefits, advantages, solutions to problems, and any elements that may allow or facilitate any benefit, advantage, or solution are not to be construed as critical, required, or essential to the invention. The scope of the invention is to be limited only by the appended claims.

What is claimed is:

1. A device for repairing a fractured calcaneus, comprising:
    a plate having a first aperture comprising a first indentation and a second indentation;
    a cylindrical barrel extending along a first longitudinal axis from a first end to a second end, said barrel comprising a first threaded bore extending orthogonally to the first longitudinal axis, a second threaded bore extending orthogonally to the first longitudinal axis, wherein the first end of the cylindrical barrel comprises a locking tab configured to mate with the first indentation when the barrel is inserted into the first aperture and at a first rotated position, and configured to mate with the second indentation when the barrel is inserted into the first aperture at a second rotated position, wherein the second indentation is located at a position other than 180 degrees circumferentially from the first indentation;
    a first lag screw comprising threads configured to engage the threads of the first bore; and
    a second lag screw comprising threads configured to engage the threads of the second bore.

2. The device of claim 1, wherein the first bore is aligned with the locking tab.

3. The device of claim 2, wherein the second bore is aligned with the locking tab.

4. The device of claim 1, further comprising a locking cap fitted into the first aperture of the plate, over the first end of the barrel, said locking cap having an outer edge.

5. The device of claim 4, further comprising screw threads on the interior surface of the first aperture and screw threads on the outer edge of the locking cap, wherein the screw threads on the interior surface of the first aperture are configured to mate with the screw threads on the outer edge of the locking cap.

6. The device of claim 4, wherein the locking cap is press fit into the aperture.

7. The device of claim 1, wherein the plate has one or more scalloped cut outs.

8. The device of claim 1, wherein the plate has a flange on the side of the plate facing the calcaneus.

9. The device of claim 8, wherein the flange partially encircles the first aperture.

10. The device of claim 8, wherein the flange entirely encircles the first aperture.

11. The device of claim 1, wherein the first lag screw further comprises a tapered head.

12. The device of claim 11, wherein the tapered head of the first lag screw is threaded.

13. The device of claim 11, wherein the second lag screw further comprises a tapered head.

14. The device of claim 13, wherein the tapered head of the second lag screw is threaded.

15. A device for repairing a fractured calcaneus, comprising:
    a plate having a first aperture and a second aperture, said first aperture comprising a first indentation and a second indentation;
    a cylindrical barrel extending along a first longitudinal axis from a first end to a second end, said barrel comprising a first bore extending orthogonally to the first longitudinal axis, and a stepped portion at the first end, wherein the first bore is threaded, and wherein the stepped portion has a locking tab configured to mate with the first indentation when the barrel is inserted into the first aperture and at a first rotated position, and configured to mate with the second indentation when the barrel is inserted into the first aperture at a second rotated position, wherein the second indentation is located at a position other than 180 degrees circumferentially from the first indentation; and
    a first lag screw comprising a threaded shaft capable of engaging the threads of the first bore;
    wherein the stepped portion extends from a first end to a second end, wherein said locking tab extends outward from the exterior surface of the stepped portion, and wherein said locking tab extends from the first end of the stepped portion to the second end of the stepped portion; and wherein the locking tab extends to the terminal-most end of the first end of the barrel.

16. A device for repairing a fractured calcaneus, comprising:
    a plate having a first aperture and a second aperture, said first aperture comprising a first indentation and a second indentation;
    a cylindrical barrel extending along a first longitudinal axis from a first end to a second end, said barrel comprising a first bore extending orthogonally to the first longitudinal axis, and a stepped portion at the first end, wherein the first bore is threaded, and wherein the stepped portion has a locking tab configured to mate with the first indentation when the barrel is inserted into the first aperture and at a first rotated position, and configured to mate with the second indentation when the barrel is inserted into the first aperture at a second rotated position, wherein the second indentation is located at a position other than 180 degrees circumferentially from the first indentation; and
    a first lag screw extending along a second longitudinal axis, said first lag screw comprising a threaded shaft capable of engaging the threads of the first bore;
    wherein the locking tab extends to the terminal-most end of the first end of the barrel.

\* \* \* \* \*